United States Patent [19]

Tanaka et al.

[11] Patent Number: 5,210,227
[45] Date of Patent: May 11, 1993

[54] IMMUNOSUPPRESSIVE COMPOUNDS

[75] Inventors: Hirokazu Tanaka, Ibaraki, Japan; Martin E. Cooper; David K. Donald, both of Leicestershire, England

[73] Assignees: Fisons plc, England; Fujisawa Pharmaceutical Company Limited, Japan

[21] Appl. No.: 661,802

[22] Filed: Feb. 27, 1991

[30] Foreign Application Priority Data

Feb. 27, 1990 [GB] United Kingdom ................. 9004396
Apr. 27, 1990 [GB] United Kingdom ................. 9009485

[51] Int. Cl.$^5$ ......................................... C07D 309/00
[52] U.S. Cl. ..................... 549/273; 554/35; 554/69; 554/127; 554/167; 554/141; 554/158; 554/156
[58] Field of Search ................. 260/398, 415; 554/35, 554/69, 127, 167, 141, 158, 156; 514/452, 613, 659, 729, 885; 549/273

[56] References Cited

FOREIGN PATENT DOCUMENTS 0184162 6/1986 European Pat. Off. .

OTHER PUBLICATIONS

Coleman, R. et al, Heterocycles, vol. 28, #1, 1989, pp. 107–161.

Primary Examiner—José G. Dees
Assistant Examiner—Deborah D. Carr
Attorney, Agent, or Firm—Marshall, O'Toole, Gerstein, Murray & Bicknell

[57] ABSTRACT

Compounds of formula I,

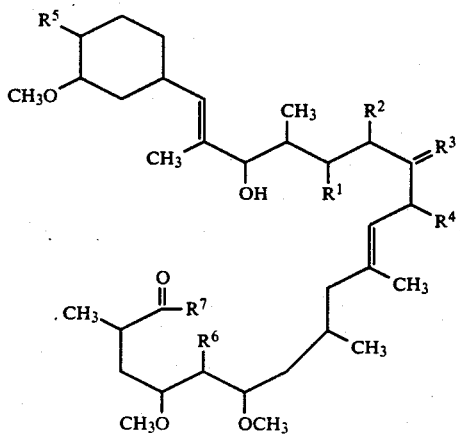

wherein $R^1$ represents H, OH, protected OH or alkoxy; $R^2$ represents H; $R^3$ represents O or (H,OH); $R^4$ represents methyl, ethyl, propyl or allyl; $R^5$ represents OH, protected OH or alkoxy; $R^6$ represents OH; $R^7$ represents OH, alkoxy or $NR^8R^9$ where $R^8$ and $R^9$ independently represent H, alkyl or aryl; in addition, $R^1$ and $R^2$ may together represent a second bond between the carbon atoms to which they are attached; and $R^6$ and $R^7$ may together represent O; and pharmaceutically acceptable salts thereof; are useful inter alia as immunosuppressive agents. The invention also provides the novel compounds of formula I.

7 Claims, No Drawings

IMMUNOSUPPRESSIVE COMPOUNDS

This invention relates to novel compounds, their use as medicaments, and compositions containing them. The invention also relates to the novel medical use of a known compound, and compositions containing it.

European Patent Application 184162 (to Fujisawa Pharmaceutical Co Ltd) discloses a number of complex immunosuppressive macrocyclic compounds isolated from microorganisms belonging to the genus Streptomyces. The macrolides are numbered FR-900506, FR-900520, FR-900523 and FR-900525, and the preparation of some of their derivatives is also described. International Patent Application WO 89/05304 (to Fisons plc) discloses a number of macrocyclic immunosuppressive compounds which may be prepared from the compounds of European Patent Application No 184162. The compounds of these two applications, and their derivatives, may be used as starting materials for production of the compounds of the present invention.

Coleman and Danishefsky [Heterocycles, 28(1), 1989] obtained fragments of the FR-900506 molecule, including 12-allyl-4,6-dimethoxy-19-[4-hydroxy-3-methoxycyclohexyl]-2,8,10,16,18-pentamethyl-5,13,15,17-tetrahydroxy-nonadeca-10,18-dienoic acid 1,5-lactone, by chemical degradation, but did not report any pharmacological activity for those fragments.

We have now surprisingly found a group of compounds which have a much simpler structure than FR-900506, and which possess immunosuppressive activity.

According to the present invention, there is provided a compound of formula I,

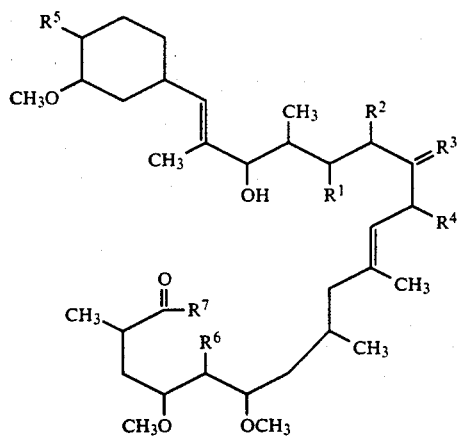

wherein
$R^1$ represents H, OH, protected OH or alkoxy;
$R^2$ represents H;
$R^3$ represents O or (H,OH);
$R^4$ represents methyl, ethyl, propyl or allyl;
$R^5$ represents OH, protected OH or alkoxy;
$R^6$ represents OH;
$R^7$ represents OH, alkoxy or $NR^8R^9$ where $R^8$ and $R^9$ independently represent H, alkyl or aryl;

in addition, $R^1$ and $R^2$ may together represent a second bond between the carbon atoms to which they are attached; and $R^6$ and $R^7$ may together represent O;

provided that when $R^1$ and $R^5$ each represent OH, $R^2$ represents H, $R^3$ represents (H,OH) and $R^4$ represents allyl, then $R^6$ and $R^7$ do not together represent O; and pharmaceutically acceptable salts thereof.

When any one of $R^1$, $R^5$ or $R^7$ represent alkoxy, we prefer them to contain from 1 to 10 carbon atoms, more preferably from 1 to 6 carbon atoms, for example methoxy or ethoxy. Similarly, when either of $R^8$ or $R^9$ represent alkyl or aryl, we prefer them to contain from 1 to 10 carbon atoms, more preferably from 1 to 6 carbon atoms, for example methyl, ethyl or phenyl.

By the term "protected OH" we mean a group which may be treated so as to yield a hydroxy group. Examples of such groups include an oxygen atom bonded to a protecting group selected from the following:

a) 1-(alkyl $C_{1-6}$ thio)alkyl $C_{1-6}$ such as alkyl $C_{1-6}$ thiomethyl (e.g. methylthiomethyl, ethylthiomethyl, propylthiomethyl, isopropylthiomethyl, butylthiomethyl, isobutylthiomethyl, hexylthiomethyl), preferably methylthiomethyl;

b) trisubstituted silyl such as tri(alkyl $C_{1-6}$)silyl (e.g. trimethylsilyl, triethylsilyl, tributylsilyl, ʰbutyl dimethylsilyl, tri-ʰbutylsilyl), (alkyl $C_{1-6}$)diaryl silyl (e.g. methyldiphenylsilyl, ethyldiphenylsilyl, propyl diphenylsilyl, ʰbutyldiphenylsilyl), preferably tri(alkyl $C_{1-6}$)silyl and (alkyl $C_{1-6}$)diphenylsilyl, most preferably ʰbutyldimethylsilyl and ʰbutyldiphenylsilyl; and c) acyl such as aliphatic acyl, aromatic acyl and aliphatic acyl substituted with aromatic groups, which are derived from carboxylic, sulphonic and carbamic acids.

Preferred protected hydroxy groups that may be mentioned include trialkylsilyloxy groups, for example ʰbutyldimethylsilyloxy.

Further protecting groups and methods for the introduction and removal of protecting groups are described in 'Protective Groups in Organic Chemistry', ed: J. W. F. McOmie, Plenum Press (1973), and 'Protective Groups in Organic Synthesis', T. W. Greene, Wiley-Interscience (1981).

A group of compounds of formula I which may be mentioned are those in which $R^4$ represents allyl or propyl.

We prefer $R^7$ to represent alkoxy.

Compounds in which $R^6$ and $R^7$ each represent OH may cyclize to the corresponding lactone compound in which $R^6$ and $R^7$ together represent O. The invention includes both forms of such compounds.

Pharmaceutically acceptable salts include salts of any carboxylic acid groups which may be present, particularly alkali metal and alkaline earth metal salts, for example sodium or calcium salts.

The invention further provides the following processes for the production of a compound of formula I as defined above, but without proviso:

(a) producing a compound of formula I in which $R^6$ and $R^7$ together represent 0, by reduction of a compound of formula II,

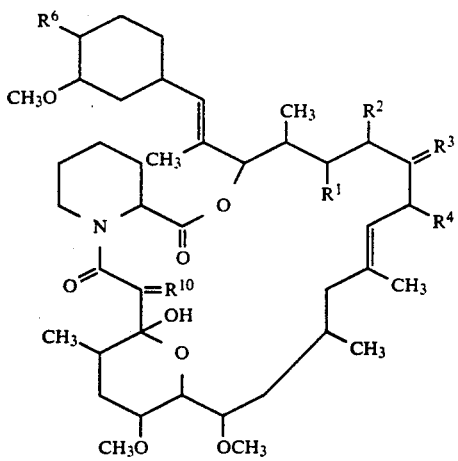

in which $R^1$ to $R^5$ are as defined above and $R^{10}$ represents O, in the presence of an amine or an acid addition salt thereof;

(b) producing a compound of formula I in which $R^6$ represents OH and $R^7$ represents alkoxy, by reduction of a compound of formula II as defined in (a) above, in the presence of an amine or an acid addition salt thereof, and an alcohol of formula $R^7H$;

(c) producing a compound of formula I in which $R^6$ and $R^7$ each represent OH, by the action of an inorganic base on a compound of formula II as defined in (a) above except that $R^{10}$ represents (H,OH);

(d) producing a compound of formula I in which $R^6$ and $R^7$ together represent O, by reaction of a corresponding compound of formula I in which $R^6$ and $R^7$ each represent OH with an esterification reagent;

(e) producing a compound of formula I in which $R^7$ represents $NR^8R^9$ by reaction of a corresponding compound of formula I in which $R^6$ and $R^7$ together represent O with an amine of formula $NHR^8R^9$;

(f) producing a compound of formula I in which $R^1$ and $R^2$ each represent H by selective reduction of a corresponding compound of formula I in which $R^1$ and $R^2$ together represent a second bond between the carbon atoms to which they are attached;

(g) producing a compound of formula I in which $R^1$ and $R^2$ together represent a second bond between the carbon atoms to which they are attached, by elimination of $H_2O$ from a corresponding compound of formula I in which $R^1$ represents OH and $R^2$ represent H;

(h) producing a compound of formula I in which one or both of $R^1$ and $R^5$ represent alkoxy by reacting a corresponding compound of formula I in which one or both of $R^1$ and $R^5$ represent OH with an alkylating agent;

(i) producing a compound of formula I in which $R^4$ represents propyl, by reduction of a corresponding compound of formula I in which $R^4$ represents allyl; and (j) producing a compound of formula I in which $R^3$ represents (H,OH) by reduction of a corresponding compound of formula I in which $R^3$ represents O.

In processes (a) and (b), the reducing agent is preferably an alkali metal cyanoborohydride, for example $NaBH_3CN$, or a tetraalkylammonium cyanoborohydride, for example $(C_4H_9)_4NBH_3CN$. The amine is preferably a primary alkylamine or an acid addition salt thereof, for example methylamine or its hydrochloride. The reaction may be carried out using a solvent, or more than one solvent using a two-phase technique, which does not adversely affect the reaction, for example water and 1,4-dioxan or water and dichloromethane at a temperature of from 0° to 50° C. In process (b), the alcohol of formula $R^7H$ may also be the solvent.

In process (c), the base is preferably an alkali metal carbonate, for example potassium carbonate. The reaction is preferably carried out using a solvent which does not adversely affect the reaction, for example methanol or ethanol, and at a temperature of from 0° to 50° C.

In process (d), suitable esterification reagents include 2-chloro-1-methylpyridinium iodide. The reaction is preferably carried using a solvent which does not adversely affect the reaction, for example dichloromethane, and at a temperature of from 0° to 50° C.

In process (e), the amine is preferably a primary alkylamine, for example methylamine. The reaction is preferably carried out using a solvent which does not adversely affect the reaction, for example methanol, and at a temperature of from 0° to 50° C.

In process (f), the reducing agent is preferably an alkyl tin hydride such as tri-$^n$butyl tin hydride, and the reaction is preferably carried out in the presence of a catalyst, such as tetrakis(triphenylphosphine)palladium(O), and optionally under slightly acidic conditions, for example in the presence of a trace of acetic acid. The reaction is preferably carried out using a solvent which does not adversely affect the reaction, for example tetrahydrofuran, and at a temperature of from 0° to 50° C.

In process (g), the elimination is preferably carried out by the action of acid, for example in the presence of a trace amount of tosic acid. The reaction is preferably carried out using a solvent which does not adversely affect the reaction, for example toluene, and at a temperature of from 50° to 100° C.

In process (h), suitable alkylating agents include alkyl tosylates, diazoalkanes and alkyl halides. The reaction is preferably carried out using a solvent which does not adversely affect the reaction, for example dichloromethane. The reaction is preferably carried out at a temperature of from 0° to 50° C.

In process (i), the reduction is preferably catalytic. Suitable catalysts include platinum catalysts (for example platinum black, platinum oxides), palladium catalysts (for example palladium oxide, palladium on charcoal), nickel catalysts (for example nickel oxide, Raney nickel), and rhodium catalysts (for example rhodium on alumina). Suitable solvents are those which do not adversely affect the reaction, and include methanol, ethanol, ethyl acetate, dichloromethane and dimethylformamide. The reaction is preferably carried out at a temperature of from 0° to 50° C.

In process (j), suitable reducing agents include sodium borohydride, zinc in acetic acid, sodium triacetoxyborohydride in acetic acid, L-Selectride (Registered Trade Mark) in tetrahydrofuran, or preferably borane/$^t$-butylamine complex in a solvent such as methanol or ethanol. The reaction is preferably carried out at a temperature of from 0° to 50° C.

The compounds of formula I may be isolated from their reaction mixtures using conventional techniques.

The compounds of formula I may alternatively be produced by total synthesis.

The compounds of formula I are useful because they possess pharmacological activity in human and non-human animals; in particular they are useful because they possess immunosuppressive activity, for example as demonstrated in the tests set out in Tests A, B and C below. Thus the compounds are indicated for use in the treatment or prevention of resistance to transplanted organs or tissues, such as kidney, heart, lung, bone marrow, skin and cornea; and of autoimmune, inflammatory, proliferative and hyperproliferative diseases, and of cutaneous manifestations of immunologically-mediated diseases: for example rheumatoid arthritis, lupus erythematosus, systemic lupus erythematosus, Hashimoto's thyroiditis, multiple sclerosis, myasthenia gravis, type 1 diabetes, uveitis, nephrotic syndrome, psoriasis, atopical dermatitis, contact dermatitis and further *eczematous dermatitides, seborrheic dermatitis, Lichen planus*, Pemphigus, *bullous Pemphigoid, Epidermolysis bullosa*, urticaria, angioedemas, vasculitides, erythemas, *cutaneous eosinophilias, Alopecia areata, eosinophilic fasciitis* and atherosclerosis.

The compounds of the invention are also indicated in the treatment of respiratory diseases, for example reversible obstructive airways disease.

Further, the compounds of the invention are indicated in the treatment of a disease selected from intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gasto-intestinal tract, for example migraine, rhinitis and eczema.

The compounds of the invention are also indicated for use as antimicrobial agents, and thus may be used in the treatment of diseases caused by pathogenic microorganisms and the like.

We therefore provide the use of a compound of formula I as defined above, but without proviso, for use as a medicament. Further, we provide the use of a compound of formula I as defined above, but without proviso, in the manufacture of an immunosuppressive agent.

For the above-mentioned therapeutic uses the dosage administered will, of course, vary with the compound employed, the mode of administration, the treatment desired (e.g. topical, parenteral or oral) and the disease indicated. However, in general, satisfactory results are obtained when the compounds are administered at a daily dosage of from 0.01 to 200 mg per kg of animal body weight.

For man the indicated total daily dosage is in the range of from 0.1 mg to log and preferably from 5 mg to 1 g, which may be administered, for example twice weekly, or in divided doses from 1 to 6 times a day or in sustained release form. Thus unit dosage forms suitable for administration, e.g. oesophageally, comprise from 0.1 mg to 5 g, and preferably 5 mg to 1 g of the compound preferably admixed with a solid or liquid pharmaceutically acceptable diluent, carrier or adjuvant.

According to the invention there is further provided a pharmaceutical composition comprising preferably less than 80%, and more preferably less than 50% by weight, of a compound of formula I as defined above, but without proviso, in combination with a pharmaceutically acceptable adjuvant, diluent or carrier. Examples of suitable adjuvants, diluents or carriers are: for tablets, capsules and dragees—microcrystalline cellulose, calcium phosphate, diatomaceous earth, a sugar such as lactose, dextrose or mannitol, talc, stearic acid, starch, sodium bicarbonate and/or gelatin; for suppositories—natural or hardened oils or waxes; and for inhalation compositions—coarse lactose. The compound of formula I preferably is in a form having a mass median diameter of from 0.01 to 10 μm. The compositions may also contain suitable preserving, stabilising and wetting agents, solubilisers (e.g. a water-soluble cellulose polymer such as hydroxypropyl methylcellulose, or a water-soluble glycol such as propylene glycol), sweetening and colouring agents and flavourings. The compositions may, if desired, be formulated in sustained release form.

For the treatment of reversible obstructive airways disease, we prefer the compound of formula I to be administered by inhalation to the lung, especially in the form of a powder.

According to a further aspect of the invention, there is provided a method of effecting immunosuppression which comprises administering a therapeutically effective amount of a compound of formula I as defined above, but without proviso, to a patient.

The compounds of formula I have the advantage that they are less toxic, more efficacious, are longer acting, have a broader range of activity, are more potent, are more stable, produce fewer side effects, are more easily absorbed, are more soluble or have other more useful pharmacological properties, than compounds previously used in the therapeutic fields mentioned above.

The compounds of formula I have a number of chiral centres and may exist in a variety of stereoisomers. The invention provides all optical and stereoisomers, as well as racemic mixtures. The isomers may be resolved or separated by conventional techniques.

The preferred stereochemistry of various chiral carbon atoms are shown in formula Ia,

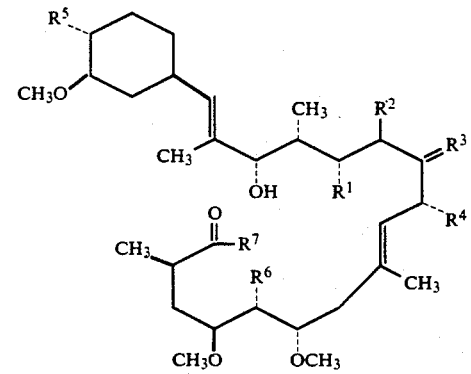

wherein $R^1$ to $R^7$ are as defined above.

TEST A

Mixed Lymphocyte Reaction (MLR) I

The MLR test was performed in microtitre plates, with each well containing $5 \times 10^5$ C57BL/6 responder cells (H-$2^b$), $5 \times 10^5$ mitomycin C treated (25 μg/ml mitomycin C at 37° C. for 30 minutes and washed three times with RPMI 1640 medium) BALB/C stimulator cells (H-$2^d$) in 0.2ml RPMI 1640 medium supplemented with 10% fetal calf serum, 2 mM sodium hydrogen carbonate, penicillin (50 μg/ml) and streptomycin (50 μg/ml). The cells were incubated at 37° C. in a humidified atmosphere of 5% carbon dioxide and 95% of air for 68 hours and pulsed with $^3$H-thymidine (0.5 μCi) 4 hours before the cells were collected. The test compound was dissolved in ethanol and further diluted in RPMI 1640 medium and added to the cultures to give final concentrations of 0.1 μg/ml or less.

TEST B

Mixed Lymohocyte Reaction (MLR) II

The MLR test was performed in 96-well microtitre plates with each well containing $3 \times 10^5$ cells from each of two responding donors in a final volume of 0.2 ml RPMI 1640 medium supplemented with 10% human serum, L-glutamine and penicillin/streptomycin. The compound under test was dissolved at 10 mg/ml in ethanol and further diluted in RPMI 1640. The cells were incubated at 37° C. in a humidified atmosphere at 5% carbon dioxide for 96 hours. $^3$H-thymidine (0.5 $\mu$Ci) was added for the final 24 hours of the incubation to provide a measure of proliferation.

TEST C

Graft versus Host Assay (GVH)

Spleen cells from DA and DAxLewis F1 hybrid rats were prepared at approximately $10^8$ cells/ml. 0.1 ml of these suspensions were injected into the rear footpads of DAxLewis F1 rats (left and right respectively). Recipient animals were dosed with the compound under test, either orally or subcutaneously, on days 0-4. The assay is terminated on day 7 when the popliteal lymph nodes of the animals are removed and weighed. The increase in weight of the left node relative to the weight of the right is a measure of the GVH response.

The invention is illustrated, but in no way limited, by the following Examples.

EXAMPLE 1

Methyl 12-allyl-4,6-dimethoxy-19-[4-hydroxy-3-methoxy cyclohexyl]-13-oxo-2,8,10,16,18-pentamethyl-5,15,17-trihydroxy-nonadeca-10,18-dienoate Methylamine hydrochloride (42 mg, 0.62 mmol) was dissolved in anhydrous methanol (2 ml), and a solution of sodium hydroxide (16 mg) in methanol (0.83 ml) was added. The resulting solution was added to macrolide FR-900506 (100 mg, 0.12 mmol) followed by a solution of sodium cyanoborohydride (7.5 mg, 0.12 mmol) in methanol (0.41 ml). The mixture was stirred for 1.5 hours at 20° C., and then concentrated in vacuo. Flash chromatography on silica eluting with ethyl acetate then gave the title compound (20 mg).

$^{13}$C NMR δ: (1:1 mixture of hemiacetal [h] formed between C13 and C17, and open chain compound [o]) 211.9 (C13, o); 177.3 (C1, o); 99.05 (C13, h); 79.5 (C5, h and o); 78.4 (C17, o); 68.4 (C17, h); 52.7 (C12, o); 57.5 (C38, h and o); 48.9 (C12, h); 18.52 (C30, o); 18.47 (C30, h); 10.6 (C27, h); 5.7 (C27, o).

MS (FAB): 629 [M+Na]$^+$.

EXAMPLE 2

Methyl 12-allyl-4,6-dimethoxy-19-4-hydroxy-3-methoxy cyclohexyl]-2,8,10,16,18-oentamethyl-5,13,15,17-tetrahydroxy-nonadeca-10,18-dienoate 4.94 ml of a solution of sodium hydroxide (150 mg, 3.74 mmol) in methanol was added to methylamine hydrochloride (421 mg, 6.23 mmol). After 5 minutes, sodium cyanoborohydride (78 mg, 1.25 mmol) in methanol (3 ml) was added, followed by a solution of macrolide FR-900506 (1 g, 1.25 mmol) in methanol (7 ml). The mixture was stirred at 20° C. for 40 minutes. Water (50 ml) was then added, followed, by brine (10 ml) and the mixture was extracted with dichloromethane (2×75 ml). The combined organic extracts were dried (Na$_2$SO$_4$) and evaporated. Flash chromatography in silica eluting with dichloromethane/acetonitrile [1:1] then ethyl acetate yielded the title compound.

$^{13}$C NMR δ: 177.37 (C1); 79.46 (C5); 73.54, 72.82, 72.5 (C23, C4, C13); 51.50 (C38); 44.04 (C12); 18.49 (C30); 5.09 (C22).

MS (FAB): 694 [M+Na]$^+$.

EXAMPLE 3

Methyl 12-allyl-5,17-dihydroxy-4,6-dimethoxy-19-[4-hydroxy-3-methoxycyclohexyl1-13-oxo-2,8,10,16,18-oentamethyl-nonadeca-10,14,18-trienoate 1.69 ml of a solution of sodium hydroxide (30 mg, 2.44 mmol) in methanol was added to methylamine hydrochloride (84 mg, 1.24 mmol). Sodium cyanoborohydride (15.6 mg, 0.25 mmol) in methanol (0.4 ml) was then added, followed by 17-allyl-1-hydroxy-12-[2-(4--hydroxy-3-methoxycyclohexyl)-1-methylvinyl)-23,25-dimethoxy-13,19,21,27-tetramethyl-11,28-dioxa-4-azatricyclo[22.3.1.0$^{4,9}$]octacosa-14,18-diene-2,3,10,16-tetraone (the compound of Example 14, European Patent Application No 323042)(200 mg, 0.25 mmol) in methanol (5 ml). The mixture was stirred at 20 C for 40 minutes. Evaporation without warming yielded a solid residue which was extracted with dichloromethane (5 ml). Flash chromatography of the extracts on silica eluting with ethyl acetate yielded the crude product (50 mg). HPLC then yielded the title compound.

$^{13}$C NMR δ: 199.97 (C13); 177.56 (C1); 149.20 (C15); 51.63 (C38); 50.38 (C12); 40.20 (C16); 18.53 (C50); 14.40, 12.45 (C26, C27).

EXAMPLE 4

Methyl 12-allyl-5.17-dihydroxy-4,6-dimethoxy-19-[4-hydroxy-3-methoxycyclohexyl]-13-oxo-2,8,10,16,18-pentamethyl-nonadeca-10,18-dienoate Water (1.3 $\mu$l) was added to a solution of the title compound of Example 3 (18 mg) in tetrahydrofuran (1 ml), followed by tetrakis(triphenylphosphine) palladium (O) (1 mg). The mixture was stirred during slow addition of a solution of tributyl tin hydride (7.4$\mu$l) in tetrahydrofuran (1 ml). After stirring at 20° C. for 24 hours, the reaction mixture was diluted with water (5 ml) and extracted with ether (2×10 ml). The ethereal layer was evaporated and the residue was partitioned between dichloromethane (5 ml) and dilute sodium bicarbonate solution (5 ml). The organic phase was dried (Na$_2$SO$_4$) and evaporated. Flash chromatography on silica eluting with dichloromethane/acetonitrile [2:1] yielded the title compound (6.4 mg).

$^{13}$C NMR δ: 211.13 (C13); 177.41 (C1); 52.22 (C12); 51.56 (C38); 48.30 (C9); 39.11 (C14); 18.59 (C30); 14.16, 12.57 (C26, C26); 6.42 (C42).

EXAMPLE 5

Methyl 5,17-dihydroxy-4,6-dimethoxy-19-4-hydroxy-3-methoxy cyclohexyl]-13-oxo-2,8,10,16,18-pentamethyl-12-propyl-nonadeca-10,14,18-trienoate A solution of 17-propyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0⁴,⁹]octacosa-14,18-diene-2,3,10,16-tetraone (the compound of Example 11, European Patent Application No 323042) (480 mg, 0.61 mmol), methylamine hydrochloride (47 mg, 7 mmol), pyridine (25 μl, 0.3 mmol) and sodium cyanoborohydride (44 mg, 0.7 mmol) in methanol (25 ml) was stirred at 20° C. for 48 hours. The reaction mixture was then evaporated to 10 ml and poured into dilute hydrochloric acid (30 ml). The mixture was then extracted with dichloromethane (3×30 ml), and the organic extracts were then dried (Na$_2$SO$_4$) and evaporated to an oil. Flash chromatography on silica eluting with petroleum ether/acetone [3:1] gave the sub-title compound (253 mg). MS (FAB): 675.8 [M+Na]⁺.

EXAMPLE 6

Methyl 5,17-dihydroxy-4,6-dimethoxy-19-[4-hydroxy-3-methoxycyclohexyl]-13-oxo-2,8,10,16,18-pentamethyl-12-propyl-nonadeca-10,18-dienoate A sample of the title compound of Example 5 (220 mg) was dissolved in tetrahydrofuran (15 ml) and water (36 μl) added. This was followed by simultaneous dropwise addition of a solution of tributyl tin hydride (0.45 ml) in anhydrous tetrahydrofuran and a solution of tekrakis (triphenylphosphine)palladium (O) (30 mg) in tetrahydrofuran (5 ml) over a period of 1 hour. Further water (36μl) was added followed by a solution of tributyl tin hydride (0.45 ml) in anhydrous tetrahydrofuran (10 ml) over 30 minutes. Water (20 ml) was then added and the mixture extracted with dichloromethane (50 ml). The organic extracts were dried (Na$_2$SO$_4$) and evaporated. Flash chromatography on silica eluting with petroleum ether/acetone [3:1] then gave the title compound (186 mg).

$^{13}$C NMR δ: 212.09 (C13); 177.42 (C1), 52.26 (C12); 51.56 (C38); 48.33 (C9); 39.91 (C14); 20.46 (C32); 18.59 (C30); 14.18, 14.10, 12.54 (C26, C27, C33) MS (FAB): 677 [M+Na]⁺.

EXAMPLE 7

Methyl 12-allyl-5,17-dihydroxy-19-[3,4-dimethoxycyclohexyl]-13-oxo-2,8,10,16,18-oentamethyl-4,6,15-trimethoxy-nonadeca-10,18-dienoate Sodium hydroxide (15.2 mg, 0.38 mmol) in methanol (0.8 ml) was added to methylamine hydrochloride (38.5 mg, 0.57 mmol) and the mixture stirred for 10 minutes. A solution of 17-allyl-1-hydroxy-12-[2-(3,4-dimethoxycyclohexyl)-1-methylvinyl]-14,23,25-trimethoxy-13,19,21,27-tetramethyl-11,28-dioxa-4-azatricyclo[22.3.1.0⁴,⁹]octacos-18-ene-2,3,10,16-tetraone (the compound of Example 1, European Patent Application No 323042) (95 mg, 0.11 mmol) in methanol (2 ml) was added, followed by a solution of sodium cyanoborohydride (7.2 mg, 0.11 mmol) in methanol (0.35 ml). The reaction mixture was stirred for 1.5 hours and then evaporated to a solid. This was extracted with dichloromethane (5 ml) and the extracts were subjected to flash chromatography on silica. Elution with dichloromethane/ethyl acetate [2:1] yielded the title compound (14 mg).

$^{13}$C NMR (1:3 mixture of hemiacetal [h] formed between C13 and C17 and open chain compound [o]) 209.73 (C13, h); 177.26 (CI, h and o); 98.38 (C13, o); 83.28, 82.85 (C22, o; C23, h); 83.18, 82.76 (C22, h; C23, o); 79.59 (C5, h and o); 81.17 (C15, o); 68.24 (C17, o); 52.93 (C12, h); 51.43 (C38, h and o); 48.62 (C12, o); 48.17 (C9, h and o); 43.03 (C14, h); 18.48 (C30, h); 18.42 (C30, o); 13.64 (C26, o); 10.41 (C27, o); 7.14 (C27, h).

MS (FAB): 720 [M+Na]⁺.

EXAMPLE 8

12-Allyl-4,6-dimethoxy-19-[4-hydroxy-3-methoxycyclohexyl]-2,8,10,16,18-centamethyl-5,13,15,17-tetrahydroxy-nonadeca-10,18-dienoic acid 1,5-lactone 0.16 ml of a solution of 93.1 mg sodium hydroxide in 2 ml of water was added to methylamine hydrochloride (21.7 mg) followed by 0.23 ml of a solution of 348 mg sodium cyanoborohydride in water (0.5 ml). To this was added macrolide FR-900506 (51.6 mg) in 1,4-dioxan and the reaction mixture was allowed to stir for 90 minutes at room temperature. The reaction mixture was then diluted with water, acidified with 2M hydrochloric acid and extracted into dichloromethane. The organic extract was dried (Na$_2$SO$_4$) filtered and evaporated to a solid in vacuo. Column chromatography on silica then gave the title compound (10 mg) as a foam.

MS: 603 [M-2H$_2$O+H]⁺; 638 [M]⁺.

$^1$H NMR (CDCl$_3$) 0.74 (3H, d, J=7.5Hz, H-26); 0.91 (3H, d, J=7.5Hz, H21); 1.56 (3H, brs, H27); 1.59 (3H, d, J=1Hz, H22); 4.04 (1H, dd, J=1 and 6.5 Hz, H5); 4.15 (1H, brs, H17).

$^{13}$C NMR δ: 174.23 (C1); 33.25 (C2); 32.14 (C3); 74.30 (C4); 82.73 (C5); 78.03 (C6); 34.75 (C7); 27.19 (C8); 49.19 (C9); 134.84 (C10); 127.99 (C11); 40.09 (C12); 75.01 (C13); 33.38 (C14); 70.15 (C15); 36.41 (C16); 76.51 (C17); 133.15 (C18); 127.39 (C19); 17.12 (C20); 20.20 (C21); 16.96 (C22); 36.13 (C23); 137.64 (C24); 115.37 (C25); 11.11 (C26); 15.78 (C27); 34.98 (C28); 35.06 (C29); 84.48 (C30); 73.71 (C31); 31.42 (C32); 30.79 (C33).

EXAMPLE 9

5,17-dihydroxy-4,6-dimethoxy-19-[4-hydroxy-3-methoxycyclo hexyl]-13-oxo-2,8,10,16,18-oentamethyl-12-propyl-nonadeca-10,14,18-trienoic acid 1,5-lactone 17-Propyl-1-hydroxy-12-[2-(4-hydroxy-3-methoxycyclo hexyl)-1-methylvinyl-23,25-dimethoxy-13,19,21,27-tetramethyl-11,28-dioxa-4-azatricyclo[22.3.1.0⁴,⁹]octacosa-14,18-diene-2,3,10,16-tetraone (the compound of Example 11, European Patent Application No 323042) (620 mg, 0.787 mmole) was added to a mixture of sodium cyanoborohydride (99 mg, 1.57 mmole), 25% aqueous methylamine solution (0.97 ml, 7.87 mmole), pyridinium chloride (909 mg, 7.87 mmole) and tetrabutyl ammonium chloride (436 mg, 1.57 mmole) in water (15 ml) and dichloromethane (30 ml). The reaction mixture, after stirring for 3 days at room temperature, was diluted with diethyl ether (50 ml) and the aqueous extract was discarded. The ether extract after washing with dilute hydrochloric acid was dried (Na$_2$SO$_4$), filtered and evaporated in vacuo. Column chromatography on silica then gave the title compound as an oil (35%).

MS:603 [M-H$_2$O+H]⁺; 621 [M+H]⁺; 643 [M+Na]⁺; 705 [M+Rb]⁺.

$^{13}$C NMR δ: 50.13 (C12); 200.83 (C13); 125.07 (C14); 148.87 (C15); 33.77 (C23); 20.43 (C24); 14.62 (C25).

EXAMPLE 10

12-Allyl-4,6-dimethoxy-19-[4-hydroxy-3-methoxycyclohexyl]-13-oxo-2,8,10,16,18-oentamethyl-5,15,17-trihydroxy-nonadeca-10,18-dienoic acid 1,5-lactone To a solution of macrolide FR 900506 (53.6 mg) in dichloromethane (1 ml) was added 0.37 ml of a solution of 51 mg of tetrabutyl ammonium cyanoborohydride in dichloromethane (1 ml). 0.1 ml of an ethereal solution of methylamine (prepared by extracting 20 ml of 30% aqueous methylamine with 20 ml of diethyl ether) was then added at room temperature. 0.5 ml of the same solution was added after 2 hours at room temperature and after 24 hours the reaction mixture was chromatographed on silica to give the title compound as an oil (11.4 mg).

MS: 659 [M+Na]+.

$^{13}$C NMR 212.00 (C13); 46.07 (C14); 71.74 (C15); 135.68 (C24); 116.59 (C25).

EXAMPLE 11

5,17-dihydroxy-4,6-dimethoxy-19-4-hydroxy-3-methoxycyclohexyl]-13-oxo-2,8,10,16,18-pentamethyl-12-propyl-nonadeca-10,18-dienoic acid 1,5-lactone The title compound from Example 9 (160 mg) was dissolved in tetrahydrofuran (20 ml) and to this was added water (0.2 ml) followed by tetrakis(triphenylphosphine) palladium (O) (20 mg). Tri-n-butyl tin hydride (300 mg) was then added portionwise over 1 hour. The reaction mixture was then diluted with water (15 ml) and extracted with dichloromethane. The organic extract was dried (Na$_2$SO$_4$), filtered and evaporated in vacuo to an oil. Column chromatography on silica then gave the title compound as an oil (123 mg).

MS: 605 [M-H$_2$O]+; 645 [M+Na]+; 707 [M+Rb]+.

$^{13}$C NMR δ: 212.14 (C13); 39.14 (C14); 26.95 (C15); 33.47 (C16); 20.44 (C17); 14.14 (C25).

EXAMPLE 12

12-Allyl-5,17-dihydroxy-19-[4-hydroxy-3-methoxycyclohexyl]-13-oxo-2,8,10,16,18-oentamethyl-4,6-dimethoxy-nonadeca-10,18-dienoic acid 1,5-lactone a)

12-Allyl-5,17-dihydroxy-19-[4-hydroxy-3-methoxyciclo hexyl]-13-oxo-2,8,10,16,18-pentamethyl-4,6-dimethoxynona deca-10.18-dienoic acid A mixture of 17-allyl-1,2-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-3,10,16-trione (the compound of Example 15, European Patent Application No 323042) (2.5 g) and potassium carbonate (1.14 g) in methanol (25 ml) was stirred at ambient temperature for 1.5 hours, and then filtered. To the filtrate were added water and diethyl ether, and the separated aqueous layer was acidified with 1N hydrochloric acid. The precipitate was extracted with diethyl ether and the extract was washed with brine, dried and then concentrated in vacuo to give the crude subtitle compound.

b)

12-Allyl-5,17-dihydroxy-19-4-hydroxy-3-methoxycyclo hexyl]-13-oxo-2,8,10,16,18-oentamethyl-4,6-dimethoxynona deca-10,18-dienoic acid 1,5-lactone 1 g of the crude subtitle compound from step (a) was dissolved in dichloromethane (20 ml), and to this were added triethylamine (0.455 g) and 2-chloro-1-methylpyridinium iodide (0.574 g). The mixture was stirred at ambient temperature for 1 hour, and then washed with water, 1N hydrochloric acid, aqueous sodium bicarbonate and brine successively and then dried. The solvent was removed by evaporation in vacuo and then column chromatography on silica eluting with diethyl ether/dichloromethane/ethyl acetate [10:5:2] gave the title compound (0.397 g).

MS (FAB): 643 [M+Na]+.

$^{13}$C NMR δ: 210.9; 173.2; 138.0; 135.7; 135.4; 129.6; 124.2; 116.0; 84.1; 82.2; 80.1; 78.8; 73.3.

EXAMPLE 13

N-Methyl-12-allyl-5,17-dihydroxy-19-[4-hydroxy-3-methoxy cyclohexyl]-13-oxo-2,8,10,16,18-pentamethyl-4,6-dimethoxy nonadeca-10,18-dieneamide A sample of the title compound of Example 12 (50 mg) was dissolved in a 30% methanol solution of methylamine (2 ml). The mixture was allowed to stand at ambient temperature for 1 hour. The solvent was then evaporated under reduced pressure and the residue purified by preparative thin layer chromatography eluting with chloroform/methanol [100:8] to give the title compound (33 mg).

MS (FAB): 674 [M+Na]+.

$^{13}$C NMR δ: 210.9; 176.9; 137.7; 135.6; 135.2; 130.2; 124.0; 116.1; 84.1; 80.3; 79.9; 79.4; 77.7; 73.3.

EXAMPLE 14

The compound of Example 6 was tested according to Test B above, and found to suppress the mixed lymphocyte reaction by 50% (IC$_{50}$) at a concentration of $1 \times 10^{-7}$M.

We claim:

1. A compound of formula I, wherein
R$^1$ represents H, OH, protected OH or alkoxy;
R$^2$ represents H;
R$^3$ represents O or (H,OH);
R$^4$ represents methyl, ethyl, propyl or allyl;
R$^5$ represents OH, protected OH or alkoxy;
R$^6$ represents OH;
R$^7$ represents OH, alkoxy or NR$^8$R$^9$ where R$^8$ and R$^9$ independently represent H, alkyl or aryl;

in addition, $R^1$ and $R^2$ may together represent a second bond between the carbon atoms to which they are attached; and $R^6$ and $R^7$ may together represent O;

provided that when $R^1$ and $R^5$ each represent OH, $R^2$ represents H, $R^3$ represents (H,OH) and $R^4$ represents allyl, then $R^6$ and $R^7$ do not together represent O;

and pharmaceutically acceptable salts thereof.

2. A compound of formula I, as claimed in claim 1, wherein $R^4$ represents allyl or propyl.

3. A compound of formula I, as claimed in claim 1, wherein $R^7$ represents alkoxy.

4. A compound of formula I, as claimed in claim 1, which is:

Methyl 12-allyl-4,6-dimethoxy-19-[4-hydroxy-3-methoxy cyclohexyl]-13-oxo-2,8,10,16,18-pentamethyl-5,15,17-trihydroxy-nonadeca-10,18-dienoate, Methyl 12-allyl-4,6-dimethoxy-19-[4-hydroxy-3-methoxy cyclohexyl]-2,8,10,16,18-pentamethyl-5,13,15,17-tetrahydroxy-nonadeca-10,18-dienoate, Methyl 12-allyl-5,17-dihydroxy-4,6-dimethoxy-19-[4-hydroxy-3-methoxycyclohexyl]-13-oxo-2,8,10,16,18-pentamethyl-nonadeca-10,14,18-trienoate, Methyl 12-allyl-5,17-dihydroxy-4,6-dimethoxy-19-[4-hydroxy-3-methoxycyclohexyl]-13-oxo-2,8,10,16,18-pentamethyl-nonadeca-10,18-dienoate, Methyl 5,17-dihydroxy-4,6-dimethoxy-19-[4-hydroxy-3-methoxy cyclohexyl]-13-oxo-2,8,10,16,18-pentamethyl-12-propyl-nonadeca-10,14,18-trienoate, Methyl 5,17-dihydroxy-4,6-dimethoxy-19-[4-hydroxy-3-methoxy cyclohexyl]-13-oxo-2,8,10,16,18-pentamethyl-12-propyl-nonadeca-10,18-dienoate, Methyl 12-allyl-5,17-dihydroxy-19-[3,4-dimethoxycyclohexyl]-13-oxo-2,8,10,16,18-pentamethyl-4,6,15-trimethoxy-nonadeca-10,18-dienoate, 5,17-Dihydroxy-4,6-dimethoxy-19-[4-hydroxy-3-methoxycyclo hexyl]-13-oxo-2,8,10,16,18-pentamethyl-12-propyl-nonadeca-10,14,18-trienoic acid 1,5-lactone, 12-Allyl-4,6-dimethoxy-19-[4-hydroxy-3-methoxycyclohexyl]-13-oxo-2,8,10,16,18-pentamethyl-5,15,17-trihydroxy-nonadeca-10,18-dienoic acid 1,5-lactone, 5,17-Dihydroxy-4,6-dimethoxy-19-[4-hydroxy-3-methoxycyclohexyl]-13-oxo-2,8,10,16,18-pentamethyl-12-propyl-nonadeca-10,18-dienoic acid 1,5-lactone, 12-Allyl-5,17-dihydroxy-19-[4-hydroxy-3-methoxycyclohexyl]-13-oxo-2,8,10,16,18-pentamethyl-4,6-dimethyoxynonadeca-10,18-dienoic acid, 12-Allyl-5,17-dihydroxy-19-[4-hydroxy-3-methoxycyclohexyl]-13-oxo-2,8,10,16,18-pentamethyl-4,6-dimethyoxynonadeca-10,18-dienoic acid 1,5-lactone, or N-Methyl-12-allyl-5,17-dihydroxy-19-[4-hydroxy-3-methoxy cyclohexyl]-13-oxo-2,8,10,16,18-pentamethyl-4,6-dimethoxy nonadeca-10,18-dieneamide.

5. An immunosuppressive pharmaceutical composition comprising a compound of formula I, as defined in claim 1, and a pharmaceutically acceptable adjuvant, diluent or carrier.

6. A process for the production of a compound of formula I, as defined in claim 1 which comprises:

(a) producing a compound of formula I in which $R^6$ and $R^7$ together represent O, by reduction of a corresponding compound of formula II, in which $R^1$ to $R^5$ are as defined above and $R^{10}$ represents O, in the presence of an amine or an acid addition salt thereof;

(b) producing a compound of formula I in which $R^6$ represents OH and $R^7$ represents alkoxy, by reduction of a corresponding compound of formula II as defined in (a) above, in the presence of an amine or an acid addition salt thereof, and an alcohol of formula $R^7H$;

(c) producing a compound of formula I in which $R^6$ and $R^7$ each represent OH, by the action of an inorganic base on a compound of formula II as defined in (a) above except that $R^{10}$ represents (H,OH);

(d) producing a compound of formula I in which $R^6$ and $R^7$ together represent O, by reaction of a corresponding OH with an esterification reagent;

(e) producing a compound of formula I in which $R^7$ represents $NR^8R^9$ by reaction of a corresponding compound of formula I in which $R^6$ and $R^7$ together represent O with an amine of formula $NHR^8R^9$;

(f) producing a compound of formula I in which $R^1$ and $R^2$ each represent H by selective reduction of a corresponding compound of formula I in which $R^1$ and $R^2$ together represent a second bond between the carbon atoms to which they are attached;

(g) producing a compound of formula I in which $R^1$ and $R^2$ together represent a second bond between the carbon atoms to which they are attached, by elimination of $H_2O$ from a corresponding compound of formula I in which $R^1$ represents OH and $R^2$ represent H;

(h) producing a compound of formula I in which one or both of $R^1$ and $R^5$ represent alkoxy by reacting a corresponding compound of formula I in which one or both of $R^1$ and $R^5$ represent OH with an alkylating agent;

(i) producing a compound of formula I in which $R^4$ represents propyl, by reduction of a corresponding compound of formula I in which $R^4$ represents allyl; or (j) producing a compound of formula I in which $R^3$ represents (H,OH) by reduction of a corresponding compound of formula I in which $R^3$ represents O.

7. A method of effecting immunosuppression which comprises administering a therapeutically effective amount of a compound of formula I as defined in claim 1, to a patient.

* * * * *